(12) United States Patent
Sisken et al.

(10) Patent No.: US 7,674,239 B2
(45) Date of Patent: Mar. 9, 2010

(54) FLEXIBLE INTRODUCER SHEATH

(75) Inventors: Richard B. Sisken, West Lafayette, IN (US); Fred T. Parker, Unionville, IN (US)

(73) Assignees: Cook Incorporated, Bloomington, IN (US); Med Institute, Inc., West Lafayette, IN (US)

( * ) Notice: Subject to any disclaimer, the term of this patent is extended or adjusted under 35 U.S.C. 154(b) by 1091 days.

(21) Appl. No.: 11/273,878

(22) Filed: Nov. 15, 2005

(65) Prior Publication Data

US 2006/0155302 A1 Jul. 13, 2006

Related U.S. Application Data

(60) Provisional application No. 60/628,848, filed on Nov. 17, 2004.

(51) Int. Cl.
*A61N 1/30* (2006.01)
*A61M 27/00* (2006.01)
*A61M 31/00* (2006.01)

(52) U.S. Cl. .................. 604/19; 604/544; 604/93.01

(58) Field of Classification Search .................. 604/19, 604/523–527; 600/435
See application file for complete search history.

(56) References Cited

U.S. PATENT DOCUMENTS

| | | | |
|---|---|---|---|
| 5,176,660 A | 1/1993 | Truckai | |
| 5,378,234 A | 1/1995 | Hammerslag et al. | |
| 5,876,386 A * | 3/1999 | Samson | 604/524 |
| 5,902,290 A | 5/1999 | Peacock, III et al. | |
| 6,419,745 B1 | 7/2002 | Burkett et al. | |
| 6,589,227 B2 | 7/2003 | Sønderskov Klint | |
| 6,591,472 B1 * | 7/2003 | Noone et al. | 29/417 |
| 6,599,557 B2 | 7/2003 | Burkett et al. | |
| 6,695,915 B2 | 2/2004 | Burkett et al. | |
| 6,733,819 B2 | 5/2004 | Burkett et al. | |
| 6,786,876 B2 | 9/2004 | Cox | |
| 2002/0032408 A1 * | 3/2002 | Parker et al. | 604/103.09 |
| 2002/0058910 A1 * | 5/2002 | Hermann et al. | 604/95.04 |
| 2002/0182328 A1 * | 12/2002 | Asai et al. | 427/384 |
| 2003/0230822 A1 | 12/2003 | Bartholomew | |
| 2003/0230823 A1 | 12/2003 | Bartholomew | |
| 2004/0010243 A1 | 1/2004 | Klint | |
| 2004/0082879 A1 | 4/2004 | Klint | |
| 2004/0220549 A1 | 11/2004 | Dittman et al. | |
| 2005/0004560 A1 | 1/2005 | Cox | |

(Continued)

FOREIGN PATENT DOCUMENTS

EP 0 925 801 B1 11/2004

(Continued)

*Primary Examiner*—Nicholas D Lucchesi
*Assistant Examiner*—Ian K Holloway
(74) *Attorney, Agent, or Firm*—Brinks Hofer Gilson & Lione

(57) ABSTRACT

An introducer apparatus and a method for forming an introducer apparatus. The apparatus comprises an inner liner having a passageway extending longitudinally therethrough. A coil in a stressed, radially expanded condition is positioned longitudinally around said inner tube. A polymeric outer tube is positioned longitudinally around the coil and the inner liner, and is bonded to the inner liner through the spaces between the turns of the coil. The polymeric outer tube is formed in a manner such that it maintains the coil in its stressed radially expanded condition. In a preferred embodiment, the inner liner and outer tube comprise a polyimide.

20 Claims, 4 Drawing Sheets

U.S. PATENT DOCUMENTS

2006/0189896 A1* 8/2006 Davis et al. ................. 600/585
2006/0282041 A1* 12/2006 Melsheimer et al. ...... 604/164.1
2007/0049903 A1* 3/2007 Jansen et al. ................ 604/526

FOREIGN PATENT DOCUMENTS

| | | |
|---|---|---|
| GB | 2 379 965 A | 3/2003 |
| WO | WO 93/15872 A1 | 8/1993 |
| WO | WO 97/06845 A1 | 2/1997 |
| WO | WO 03/000116 A2 | 1/2003 |
| WO | WO 03/094794 A1 | 11/2003 |
| WO | WO 2004/069297 A1 | 8/2004 |

* cited by examiner

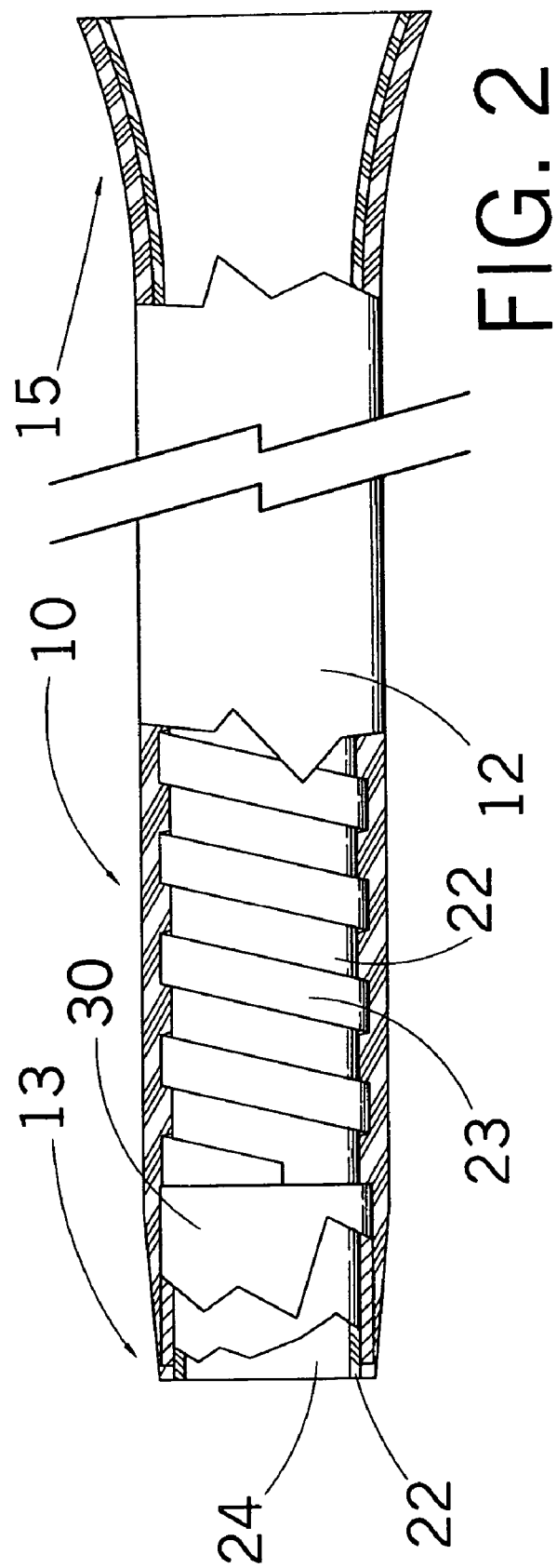

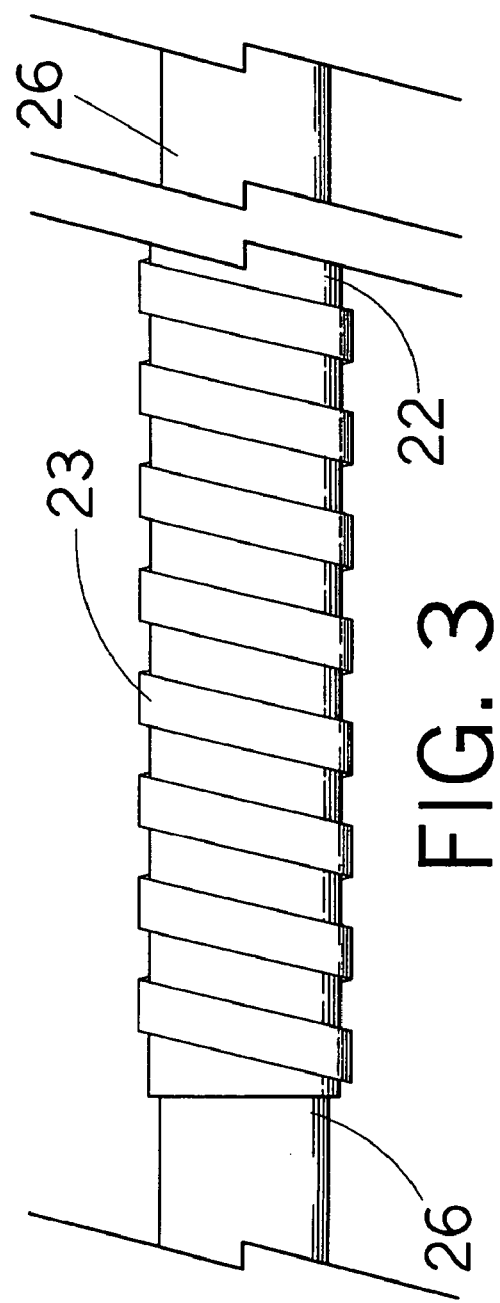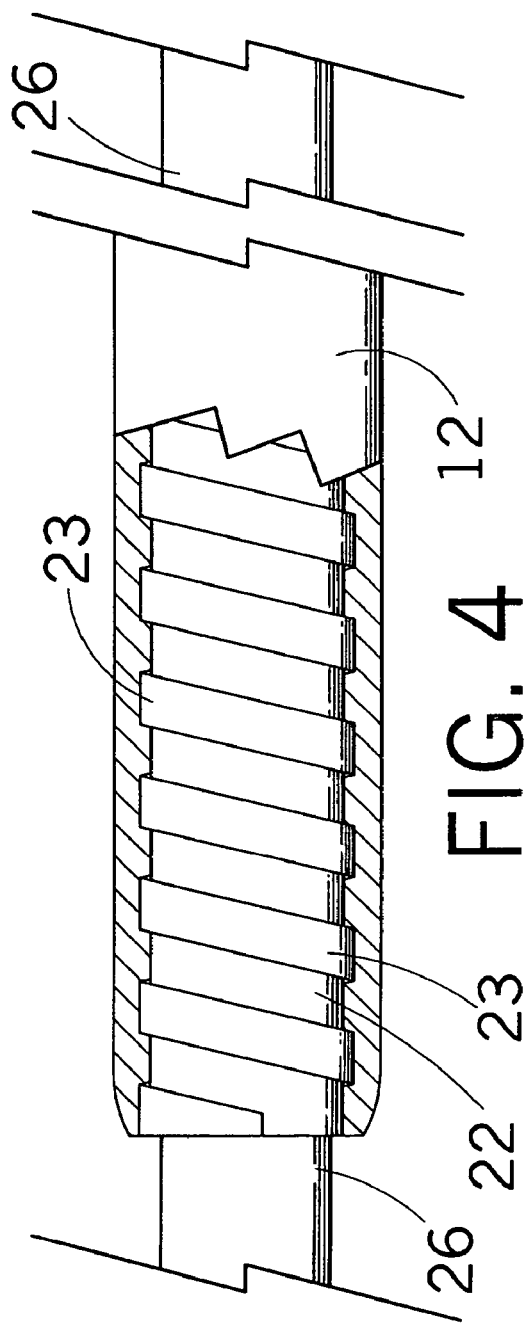

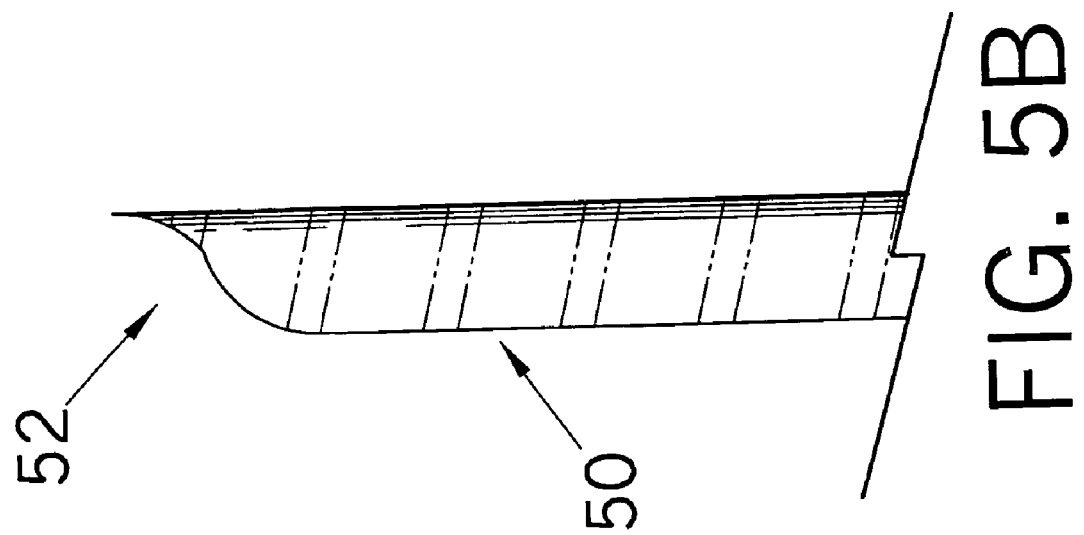
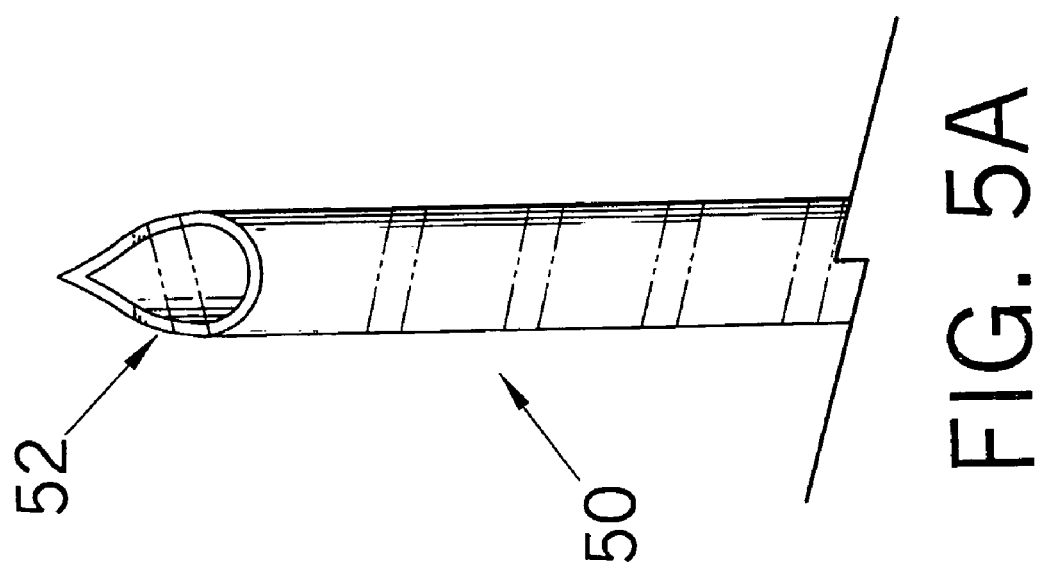

FLEXIBLE INTRODUCER SHEATH

RELATED APPLICATION

The present patent document claims the benefit of the filing date under 35 U.S.C. §119(e) of Provisional U.S. Patent Application Ser. No. 60/628,848, filed Nov. 17, 2004, which is hereby incorporated by reference.

BACKGROUND

1. Technical Field

The present invention relates to a sheath for providing vascular access. More particularly, the invention relates to a thin-walled, flexible, kink resistant introducer sheath, and a method of manufacturing a sheath.

2. Background Information

Introducer sheaths or catheters are widely used as conduits to provide percutaneous access to the vascular system. For optimal use, it is desired that such sheaths have as thin-wall construction as possible, in view of the nature of the sheath. In addition, it is desired that such sheaths be flexible and kink resistant, so that they can traverse the narrow confines of the vascular system. Further, it is desired that such sheaths be amenable to manufacture by cost effective means.

Many existing sheaths fall short of one or more of these objectives. For example, in order to improve the level of kink resistance, some manufacturers have deemed it necessary to provide a sheath having a relatively thick sheath wall. Increasing the thickness of the wall of a sheath may improve the level of kink resistance somewhat when compared to a thin-walled sheath, however the level of kink resistance may still be insufficient for some intended uses. In addition, increasing the thickness of the sheath wall is inherently undesirable, because in order to accommodate the increased size of the sheath, a larger entry opening must be made in the body vessel than would otherwise be required. On the other hand, in order to reduce the size of the entry opening required, some manufacturers provide a sheath having a relatively thin wall. However, a thin-walled sheath may adversely affect the kink resistance and the pushability of the sheath. Thus, there is generally a trade-off that must be made during construction of a sheath, so that the various desirable properties may be optimized to the greatest extent possible, consistent with the intended use of the sheath.

Sheaths used in certain medical procedures in which a fluid is to be introduced and/or removed from the vasculature of a patient, such as hemofiltration and dialysis procedures, are particularly prone to kinking. Such sheaths must remain positioned in a patient's body for an extended period of time, and as a result, are prone to being bent or pinched off. A kinked sheath is unusable, and cannot be straightened while positioned in the body of a patient. Consequently, the sheath must be removed, leaving an enlarged, bleeding opening which typically cannot be reused. Vascular access must then be re-attempted at an alternative site, and the procedure is restarted. Restarting the procedure causes a time delay, which is inconvenient, and at times may be life threatening. In addition, in some cases, an acceptable alternative site may not be readily available for introducing another sheath.

Another problem with existing introducer sheaths is that the sheath may kink when a physician attempts to insert an interventional device, such as a catheter or a stent, through the sheath during an emergency procedure. Small diameter introducer sheaths are particularly prone to being bent and kinked under the time constraints that arise during an emergency situation. If kinking occurs, the sheath becomes unusable and a new sheath must be introduced at the same or another access site.

It is desired to provide a thin-walled introducer sheath that has sufficient stiffness and kink resistance to permit it to be introduced into the vascular system to perform an interventional procedure, and that is sufficiently flexible to permit it to be directed to appropriate sites within the vasculature of a patient. It is further desired to provide a cost efficient method of making a flexible, kink resistant sheath.

BRIEF SUMMARY

The present invention has been accomplished in view of the above-mentioned technical background. It is an object of the present invention to provide a thin-walled kink resistant sheath that allows a user to readily traverse tortuous vessels in a patient's vasculature to deliver and/or remove materials or fluids without causing undue trauma to any part of the patient's body. It is a further object of this invention to provide a cost effective method for manufacturing a sheath.

In one form thereof, the invention comprises an introducer apparatus comprising a polyimide inner liner having a passageway extending longitudinally therethrough. A coil in a stressed, radially expanded condition is positioned longitudinally around the inner tube. A polymeric outer tube comprising a polyimide is positioned longitudinally around the coil and the inner liner. The outer tube is bonded to the inner liner through the spaces between the coil turns, and the polymeric outer tube maintains the coil in the stressed radially expanded condition.

In another form thereof, the invention comprises a method of making an introducer apparatus. An inner liner is positioned over a mandrel, and a coil is positioned over the inner liner. The coil is radially stretched into a stressed condition, and mounted onto the inner liner in a manner such that the coil is maintained in the radially stressed condition. A substrate comprising the mandrel, inner liner and stressed coil is inserted into a solution of a polymer, and the substrate is maintained in the polymer solution until a sufficient amount of the polymer adheres to an outer surface of the inner liner to form an outer tube, and to maintain the coil in the stressed condition. The outer tube is cured, and the mandrel is removed.

BRIEF DESCRIPTION OF THE DRAWINGS

FIG. 2 is a side view of a sheath according to an embodiment of the present invention, partially in section;

FIG. 3 is a side view of a liner and coil positioned over a mandrel;

FIG. 4 is a side view, partially in section, of the sheath of the present invention after it has been dipped into a polymeric solution and dried; and FIG. 5a is a top view and FIG. 5b is a side view of a needle formed according to an embodiment of the present invention.

DETAILED DESCRIPTION OF THE DRAWINGS AND THE PRESENTLY PREFERRED EMBODIMENTS

Figure 1:
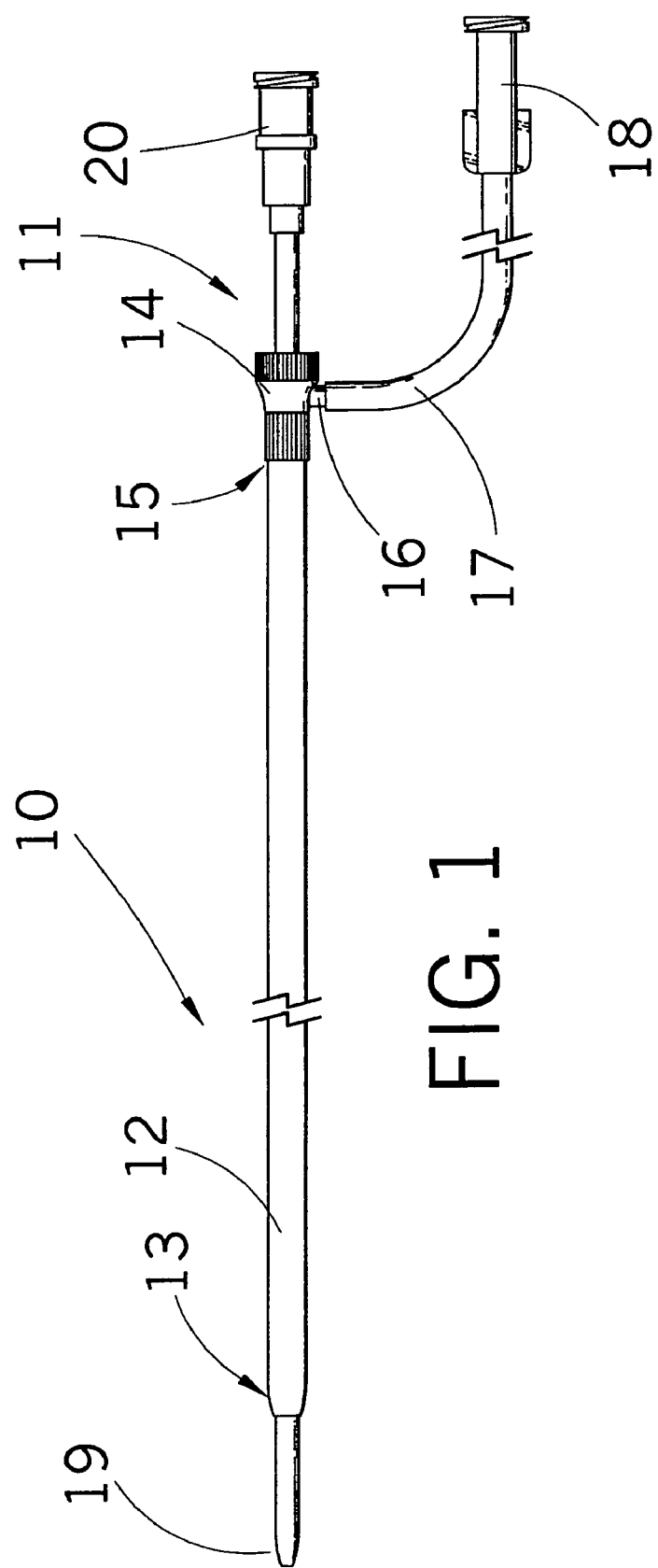
FIG. 1 is a side view of a sheath of the type described in the present invention, shown in combination with a dilator and a connector valve.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the inventive apparatus, as well as the axial ends of various component features. The term "proximal" is used in its conventional sense to refer to the end of the apparatus (or component thereof) that is closest to the operator during use of the apparatus. The term "distal" is used in its conventional sense to refer to the end of the apparatus (or component thereof) that is initially inserted into the patient, or that is closest to the patient.

FIG. 1 depicts an illustrative flexible, kink-resistant, introducer sheath 10. Sheath 10 includes a tapered distal end 13, and a flared proximal end 15. In FIG. 1 sheath 10 is shown in combination with a tapered dilator 11 that extends longitudinally through the inner passageway of the sheath. Dilator 11 includes a tapered distal end 19 for accessing and dilating a vascular access site over a wire guide in conventional fashion. The general configuration of sheath 10 visible in FIG. 1 is typical of introducer sheaths known in the art.

In the embodiment shown in FIG. 1, a connector valve 14 is also shown in combination with sheath 10. Connector valve 14 typically includes one or more silicone disks (not shown) for preventing the backflow of fluids therethrough. The disks typically include a slit or aperture to allow passage of the dilator therethrough in well-known fashion. Connector valve 14 also includes a side arm 16 to which tube 17 and male Luer lock connector 18 may be connected for introducing and/or aspirating fluids through the sheath. A conventional male Luer lock connector hub 20 is attached at the proximal end of the dilator for connection to syringes and other medical apparatus. Various side-arms, tubes, connectors and adaptors that are suitable for use with an introducer sheath are well known in the art, and may be substituted for those shown in FIG. 1.

Depicted in FIG. 2 is a partially sectioned view of an introducer sheath 10 according to an embodiment of the present invention. This sheath may be used in combination with a dilator and connector valve as shown in FIG. 1; however, for purposes of clarity, these elements have been omitted from this figure. In the embodiment shown, sheath 10 comprises an inner liner 22, a coil 23 that is wound or compression fitted around inner liner 22, and an outer layer 12. A passageway 24 extends longitudinally through inner liner 22. Outer sheath tube 12 is connected to inner liner 22 through the spacings of the coil, according to a process that will be described. An optional radiopaque marker band 30 may also be provided. Preferably, band 30 is positioned over the distal end of the inner tube next to coil 23. Typically, the radiopaque marker band is formed of a material commonly used for such purposes, such as tungsten, gold, tantalum, and the like.

Inner liner 22 preferably comprises a polyimide. Polyimides have good structural integrity, and are available in wall thicknesses as low as about 0.001 inch (0.025 mm). The structural integrity of a polyimide inner liner prevents the turns of coil 23, as well as other devices that may be in passageway 24, from protruding through the inner liner into the passageway. It is common to use more lubricious materials that have a lower coefficient of friction than polyimides, such as PTFE and other fluorocarbons, as inner liners for medical sheaths. However, polyimides have sufficient lubricity and a sufficiently low coefficient of friction to be used as a sheath liner material in most instances. In addition to its structural integrity and low wall thickness, another advantageous property of polyimide is that it is highly amenable to bonding to other materials. As a result, additional coatings can be bonded to a polyimide liner to provide additional desirable properties. One example of such a coating is a low friction internal coating that can be bonded to the inner surface of the polyimide liner in applications that demand very low friction. Outer tubular structures can likewise be very reliably bonded to the outer surface of the polyimide liner.

Preferably, inner liner 22 has a substantially uniform inner diameter that extends the entire length of passageway 24. In this manner, the largest possible diameter catheter, stent or other interventional device can be passed through the sheath. When dealing with intravascular devices it is normally desirable to utilize a sheath having the largest possible inner diameter, and the smallest possible outer diameter, that is sufficient to achieve the intended purpose. Thus, the use of a polyimide inner liner limits the thickness of the tube while, at the same time, maintaining the structural integrity of the sheath. In this regard, an inner liner having a thickness of between about 0.001 and 0.004 inch (0.025 and 0.10 mm) is preferred, and more preferably between about 0.001 and 0.002 inch (0.025 and 0.05 mm).

Coil 23 may be compression fitted or wound over inner liner 22. Preferably, coil 23 is a flat wire coil. Coil 23 may be formed from ferrous metals and alloys, such as stainless steel. Alternatively, the coil may be formed from well known fibrous materials, such as carbon fiber. As another alternative, the coil may be made from non-ferrous metallic materials, such as the nickel-cobalt base alloy known as MP-35N, the copper-nickel alloy known as MONEL, the nickel-titanium alloy known as nitinol, and similar other non-ferrous metals and alloys. Those skilled in the art will recognize that coils of compositions other than those mentioned above, and that are commonly used in medical devices, may be substituted. In addition, coils having cross-sectional dimensions other than flat wire, such as round wire, oval wire, etc., can also be substituted. However, since it is generally desired to maintain as small a cross-sectional dimension as possible, a flat wire coil is normally preferred over a round or oval wire coil.

Compatibility to magnetic resonance imaging (MRI) is often an important factor for an introducer sheath. Thus, a carbon fiber coil is particularly advantageous in these instances, since MRI compatibility with carbon fiber has been well established. A stainless steel coil is less compatible with MRI, although such compatibility is improved if sufficient spacing is provided between the coil turns to minimize the formation of eddy currents. In addition, many non-ferrous metallic materials such as those described above, are also compatible with MRI and may be preferred when MRI compatibility is a concern.

In the preferred embodiment shown in FIG. 2, the flat wire coil 23 includes uniform spacings of equal width between the turns of the coil, and the turns are provided with constant pitch. Generally, it is preferred that adjacent coil turns are spaced from each other by about 0.004 to 0.012 inch (0.10 to 0.30 mm), and more preferably, by about 0.008 inch (0.20 mm). Smaller diameter sheaths will generally have turns spaced closer together, while larger diameter sheaths will generally have turns spaced apart by a greater distance. Increasing the space between the coil turns generally increases the flexibility of a sheath, while decreasing the space between coil turns generally decreases the flexibility of the sheath. As well known by those skilled in the art, care must be taken to avoid spacing the turns apart by too great a distance. Such spacing would lessen the amount of support provided for the sheath, and increase the possibility of kinking. Those skilled in the art may readily determine proper spacing of coil turns for a particular application.

To further advantageously control the flexibility and kink-resistance of the delivery catheter and sheath, the width and thickness of the flat wire coil can be varied. Preferably, each turn of the flat wire coil has a width (measured in the longitudinal direction of the sheath) ranging between about 0.004 and 0.012 inch (0.10 to 0.30 mm), and more preferably between about 0.006 and 0.008 inch (0.15 and 0.20 mm). In addition, the flat wire coil preferably has a thickness ranging between about 0.001 and 0.003 inch (0.025 and 0.075 mm), and more preferably about 0.002 inch (0.05 mm). Generally speaking, narrower and/or thinner coils result in greater flexibility while wider and thicker coils result in lesser flexibility.

Although the turns of the coil shown in the preferred embodiment of FIG. 2 have uniform spacing and a constant pitch, this need not be the case. If desired for a particular application, the coil may be provided with non-uniform spacings of the coil turns, i.e., the pitch of the coil turns may be varied at discrete portions of the coil. Such variance may be desired, for example, when it is desired to provide a particular segment of the coil with a flexibility that differs from the flexibility of another segment of the coil. For example, a sheath or shaft might be produced that has a very strong proximal section for pushability outside the patient, while having more flexibility at the distal end. In this case, the coil turns at the distal end would be spaced a greater distance apart than the coil turns at the proximal end. In addition, a gradual transition in stiffness may be provided by varying the coil spacing in a controlled and consistent manner from highly spaced to lesser spaced.

Preferably, the respective coil ends are spaced from the respective distal and proximal ends of the inner tube. This spacing permits tapering and flaring of the respective distal and proximal ends of the sheath. In a conventional configuration in which a valve is attached at the proximal end of the sheath and a tapered tip formed at the distal end, the coil may be terminated between about 0 and 0.25 inch (0 and 6.35 mm) from the proximal end of the sheath, and between about 0 and 0.05 (0 and 1.3 mm) from the distal end. These dimensions are only examples, and those skilled in the art will appreciate that other dimensions may be selected for a particular application.

Preferably, the coil is maintained in the sheath in a stressed condition. It is generally known to maintain coils in a stressed condition, and any of the means known in the art for maintaining such a condition may be utilized. One particularly preferred way of stressing the coil will be discussed hereinafter in conjunction with a description of the inventive process of manufacturing a coil.

Outer tube 12 can be formed of any well-known polymer commonly used for such purpose. Preferably, when inner liner 22 comprises a polyimide, outer tube 12 also comprises a polyimide. Since both the inner liner and the outer layer comprise a polyimide in this preferred embodiment, the bonding between them is very satisfactory for use as a sheath. In addition, due to the structural integrity of polyimides, the layers can be made very thin. Preferably, the outer layer has a thickness between about 0.001 and 0.004 inch (0.025 and 0.10 mm), and more preferably, between about 0.001 and 0.002 inch (0.025 and 0.05 mm). Although it is preferred that the outer layer be formed of a polyimide, this need not necessarily be so. Those skilled in the art will appreciate that other known materials, such as nylon and TFE, can be used for a particular application, provided that satisfactory bonding and structural integrity is provided for the desired application.

When inner liner 22 and outer tube 12 are both formed from polyimides, they need not comprise the same polyimide in all instances. In most cases it will be desirable to utilize the same or a structurally similar polyimide in each of inner liner 22 and outer tube 12. This is due to the enhanced boding that occurs between identical or structurally similar polymers. When polyimides are to be utilized, those skilled in the art may readily select appropriate polyimides that are sufficiently compatible, and that are sufficiently bondable for a particular application.

The structure of sheath 10 should, of course, be sufficiently flexible so that the sheath can navigate the particular pathways expected to be encountered in the vasculature. If desired, outer tube 12 can comprise two or more tube segments of varying durometer. When multiple segments of different durometers are used in a sheath, the segments will generally be aligned in order of decreasing durometer (increasing flexibility) from the proximal end to the distal end of the sheath. Frequently, multiple durometer tube segments are employed when tortuous pathways must be traversed.

A preferred method for preparing sheath 10 will now be described. Initially, inner liner 22 is fitted over a suitably-sized mandrel 26. Coil 23 is then compression fitted or wound around inner tube 22 (FIG. 3). Suitable techniques for compression fitting and winding a coil around a tube are well known in the art, and are described, for example, in U.S. Pat. No. 5,380,304, incorporated by reference herein. Preferably coil 23 is initially expanded in the radial direction, and the axial ends of the coil in its expanded condition are clipped or otherwise manipulated to engage respective axial ends of the inner liner or the mandrel, such as by use of a conventional clip, clamp or like device. The coil may be expanded by simply making a small twist of the coil in the unwinding direction. The amount of the twist should be limited to avoid a spiraling effect that may occur if too great a twist is made. In this way, the coil is maintained in the expanded condition during formation of the sheath. If present, radiopaque marker tube 30 can be positioned over the inner tube adjacent the distal end of the coil.

The entire structure may then be dipped in a bath of polyimide resin to form outer layer 12. Polyimide from the resin bath permeates between the turns of coil 23, and bonds to the outer surface of inner liner 22 (FIG. 4). The structure is then cured by heating in an oven. The outer tube 12 is essentially self-leveling after dipping and curing, which provides a substantially uniform outer diameter to the tube. Once outer tube 12 has cured, the mandrel and the clips are removed. The coil is then maintained in the sheath in the expanded condition.

The inventive sheath may be formed to have a very low wall thickness, such as about 0.004 inch (0.10 mm). Preferably, the wall thickness of the sheath is between about 0.004 and 0.006 inch (0.10 and 0.15 mm).

With the inventive sheath, flexibility is maintained with only limited exposure to kinking. The process of coiling directly onto the inner liner and maintaining the coil in a compressed condition when the outer layer is applied enables the sheath to maintain the residual stress of the coil, since the coil retains its inherent urge to spring larger. This structure thus presents a pre-stress condition that maintains the strength of the structure and its resistance to kinking.

If desired, the outer tube can be beveled or ground to provide a tapered distal end that enables a delivery catheter tube to more easily traverse the vasculature of a patient. Furthermore, if desired, a hydrophilic coating may be applied to the outer surface of the sheath. A hydrophilic coating increases the lubricity of the catheter when compared to non-coated catheters, and allows for ease of insertion and/or removal of the catheter. The coating may be applied to the entire outer surface of the sheath, or to a section of the outer surface, such as the distal-most section, if it is desired to increase the lubricity of only a portion of the outer surface. Other details of the construction of the sheath are conventional, many of which are discussed in the incorporated-by-reference U.S. Pat. No. 5,380,304.

In addition to forming an introducer sheath, the teachings of the present invention may also be utilized to form other medical devices. For example, an ultra stiff shaft could be prepared and sharpened sufficiently to produce an MRI-compatible needle. For this application, the coil turns would be closely spaced, and the coil itself will normally be wider (i.e., in terms of the aspect ratio of the cross section of the individual coil turns) than when the coil is used in an introducer sheath.

FIGS. 5a and 5b are top and side views, respectively, of a tri-beveled needle 50, formed according to the teachings of the present invention. Preferably, the needle comprises a polyimide body as described previously. There is always a gap 52 present when sectioning a spiral structure, but the gap (to be supported by polyimide alone) would be in a low-stress portion of the needle tip, as shown in FIGS. 5a and 5b.

It is therefore intended that the foregoing detailed description be regarded as illustrative rather than limiting, and that it be understood that it is the following claims, including all equivalents, that are intended to define the spirit and scope of this invention.

The invention claimed is:

1. An introducer apparatus, comprising:
   an inner liner having a passageway extending longitudinally therethrough, said passageway having a substantially uniform diameter, said inner liner comprising a polyimide;
   a coil in a stressed, expanded condition, said coil comprising a plurality of turns positioned longitudinally around said inner tube, said turns having a predetermined spacing therebetween; and
   a polymeric outer tube positioned longitudinally around said coil and said inner liner and bonded to said inner liner through the spaces between said turns;
   wherein the polymeric outer tube maintains the coil in said stressed radially expanded condition.

2. The introducer apparatus of claim 1, wherein said outer tube comprises a polyimide.

3. The introducer apparatus of claim 2, wherein said inner liner passageway has a substantially uniform diameter.

4. The introducer apparatus of claim 3, wherein said inner liner has a thickness between about 0.001 and 0.004 inch (0.025 and 0.10 mm).

5. The introducer apparatus of claim 4, wherein said inner liner has a thickness of about 0.001 inch (0.025 mm).

6. The introducer apparatus of claim 3, wherein said coil turns are spaced apart a substantially uniform distance.

7. The introducer apparatus of claim 6, wherein said coil turns are spaced from each other by about 0.008 inch (0.20 mm).

8. The introducer apparatus of claim 6, wherein said coil comprises flat wire.

9. The introducer apparatus of claim 8, wherein said flat wire has a thickness between about 0.001 and 0.003 inch (0.025 and 0.075 mm).

10. The introducer apparatus of claim 2, wherein both the inner liner and the outer tube comprise the same polyimide composition.

11. The introducer apparatus of claim 2, wherein at least the distal end of the outer surface of said introducer apparatus is coated with a hydrophilic compound.

12. The introducer apparatus of claim 2, wherein said apparatus has a wall thickness of about 0.004 inch (0.10 mm).

13. A method of making an introducer apparatus, comprising the steps of:
    positioning an inner liner over a mandrel;
    positioning a coil over said inner liner;
    radially stretching the coil into a stressed condition, and mounting the coil to one of said inner liner and said mandrel to maintain the coil in the radially stressed condition;
    inserting a substrate comprising said mandrel, said inner liner and said stressed coil into a solution of a polymer, and maintaining said substrate in said polymer solution until a sufficient amount of said polymer adheres to an outer surface of said inner liner to form an outer tube, and to maintain the coil in the stressed condition;
    curing said outer tube; and
    removing said mandrel.

14. The method of claim 13, wherein at least one of the inner liner and the outer tube comprises a polyimide.

15. The method of claim 13, wherein both the inner liner and the outer tube comprise a polyimide.

16. The method of claim 13, wherein said inner liner comprises a polyimide, and said polymer solution comprises a polyimide bath.

17. The method of claim 16, wherein said coil is mounted to one of the inner liner and mandrel by clipping the axial ends of the stressed coil to said liner or mandrel.

18. The method of claim 13, wherein said curing step takes place in an oven.

19. The method of claim 13, wherein said inner liner has a thickness of about 0.001 inch (0.025 mm).

20. The method of claim 14, wherein said apparatus has a wall thickness of about 0.004 inch (0.10 mm).

* * * * *